(12) United States Patent
Nussinovitch

(10) Patent No.: US 6,589,328 B1
(45) Date of Patent: *Jul. 8, 2003

(54) SPONGES OF HYDROCOLLOIDS

(75) Inventor: Amos Nussinovitch, Petah-Tiqua (IL)

(73) Assignee: Yissum Research Development Company of The Hebrew University of Jerusalem, Jerusalem (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/877,804

(22) Filed: Jun. 18, 1997

Related U.S. Application Data

(63) Continuation-in-part of application No. 08/491,983, filed as application No. PCT/EP94/00107 on Jan. 17, 1994, now abandoned.

(30) Foreign Application Priority Data

Jan. 19, 1993 (IL) .................................................. 10441

(51) Int. Cl.$^7$ .............................. A23L 1/04; A23B 4/04
(52) U.S. Cl. ............... 106/205.1; 106/122; 106/162.81; 106/206.1; 426/44; 426/60; 426/62; 426/77; 426/78; 426/84; 426/103; 426/138; 426/279; 426/282; 426/283; 426/445; 426/551; 426/559; 426/561; 426/564; 426/573; 426/576; 426/650; 426/652; 426/653; 426/658; 426/661; 426/446; 426/447; 426/498; 426/808
(58) Field of Search .............................. 426/84, 60, 62, 426/77, 78, 103, 138, 279, 282, 283, 445, 551, 559, 561, 564, 573, 576, 650, 652, 653, 658, 661, 446, 447, 498, 808; 106/205.1, 206.1

(56) References Cited

U.S. PATENT DOCUMENTS 4,064,282 A * 12/1977 Hallstrom et al. .......... 426/559
4,292,972 A * 10/1981 Pawelchak et al. ......... 128/296

OTHER PUBLICATIONS

Chemical Abstracts 96:5138, "Sponge–andDough Bread", Kilborn et al., 1981.*

* cited by examiner

*Primary Examiner*—Frederick Krass
(74) *Attorney, Agent, or Firm*—Eitan, Pearl, Latzar & Cohen-Zedek

(57) ABSTRACT

The invention provides sponges (foams) produced from hydrocolloids by the expansion of gels of these. The foams have properties which can be varied, such as water absorption, biodegradibility, pore size and structure. Edible products can be produced which may contain an edible plasticizer, a sugar or sugar substitute and possibly also a flavoring agent or taste enhancer. The novel sponges are produced by preparing a gel of a hydrocolloid, and either sealing it in a closed vessel with a liquid of similar composition, pressurizing the vessel and abruptly releasing the pressure, followed by freeze drying, or by incorporating in such a gel a suitable microorganism, such as a yeast and inducing fermentation in the presence of a suitable nutrient medium, so that the carbon dioxide formed results in the expansion and foam formation, which is processed to the final product. The sponges-foams of the invention are such, that the initial network of the gel is maintained.

11 Claims, 15 Drawing Sheets

SPONGES OF HYDROCOLLOIDS

This is a Continuation-In-Part Application of application Ser. No. 08/491,983, filed Jul. 18, 1995, now abandoned, which is a 371 of PCT/EP94/00107, filed Jan. 17, 1994.

FIELD OF THE INVENTION

The invention relates to novel sponges which have a variety of textures, structures, water absorbing properties and biodegradability. Certain sponges of the invention can be used as edibles, and there can be produced low- high and ultra-high-calorie content sponges. The latter are of special value where highly concentrated edibles are required. Certain types of sponges can be used in medicine and also in a variety of industries. Sponges according to the invention can be used in diapers, hygienic pads, packaging material and the like.

BACKGROUND OF THE INVENTION

There is known a wide variety of spongy organic and inorganic materials. There are known open-cell sponges and closed-cell ones. According to the present invention there can be provided edible sponges and sponges for a variety of uses, with controlled properties.

A cellular solid is an interconnected network of solid struts or plates which form the edges and faces of cells (Gibson and Ashby, 1988). Cellular materials such as cork whose first reported use was as bungs in wine bottles in Roman times, and other similar solids have been used for centuries. Recently, a variety of man-made cellular solids have been developed. They include honeycomb-like materials, and polymeric foams which are used in everyday life for the production of disposable coffee cups for example, to construction of crash padding in an aircraft cockpit. Foaming techniques for polymers, metals, ceramics and glasses exist. These foams can be used for insulation, cushioning and absorbing the impact of kinetic energy.

The structure of cellular solids ranges from the near-perfect order of the bee's honeycomb to the disordered, three-dimensional networks of sponges and foams (Gibson and Ashby, 1988). There is a clear distinction between open-cell edges and closed-cell foams. In the first, the solid material has been drawn into struts which form the cell edges. In closed cells, solid membranes close off the cell faces, but the solid is rarely uniformly distributed between the edges and faces. When foaming takes place, surface tension can be a dominant force responsible for drawing the solid material into the cell edges, leaving a thin cell face framed by thicker edges. If surface tension shapes the structure, four edges meet at 108° angles at each vertex, and three faces meet at 120°. Metal, ceramic and glass foams are good examples of this type of structure.

Many foods are solid foams. Bread usually has closed cells, expanded by the fermentation of yeast or by $CO_2$ from bicarbonate. Meringue is a foamed egg white with sugar. Foamed chocolate is an example of a food expanded to change its texture. Other hard brittle candies are also often expanded to make them attractive to consumers or if they are sold by volume, to make them cheaper. Other important "solid-foam" foods are breakfast cereals and snack foods, which are foamed with steam to produce texture and crunchiness.

Nussinovitch et al. (1993) have demonstrated the production of mechanically stable solid sponges by immersing bicarbonate-containing agar and alginate gels in an acid bath, causing them to form internal gas bubbles, then freeze-drying them. These sponges exhibit characteristic compressive stress-strain curves and their properties are largely dependent on the conditions of their preparation.

The invention demonstrates that it is possible to create hydrocolloid sponges, by a variety of methods. Different, unrelated techniques are described here in addition to a procedure to change the structure and porosity of sponges. Another aim of the research was to show that stress-strain relationships in sponges can be successfully described by a three-parameter model originally developed for polymeric sponges and baked goods and that these sponges, because of their different inherent properties, could have potential uses in many different fields.

SUMMARY OF THE INVENTION

Figure 1:
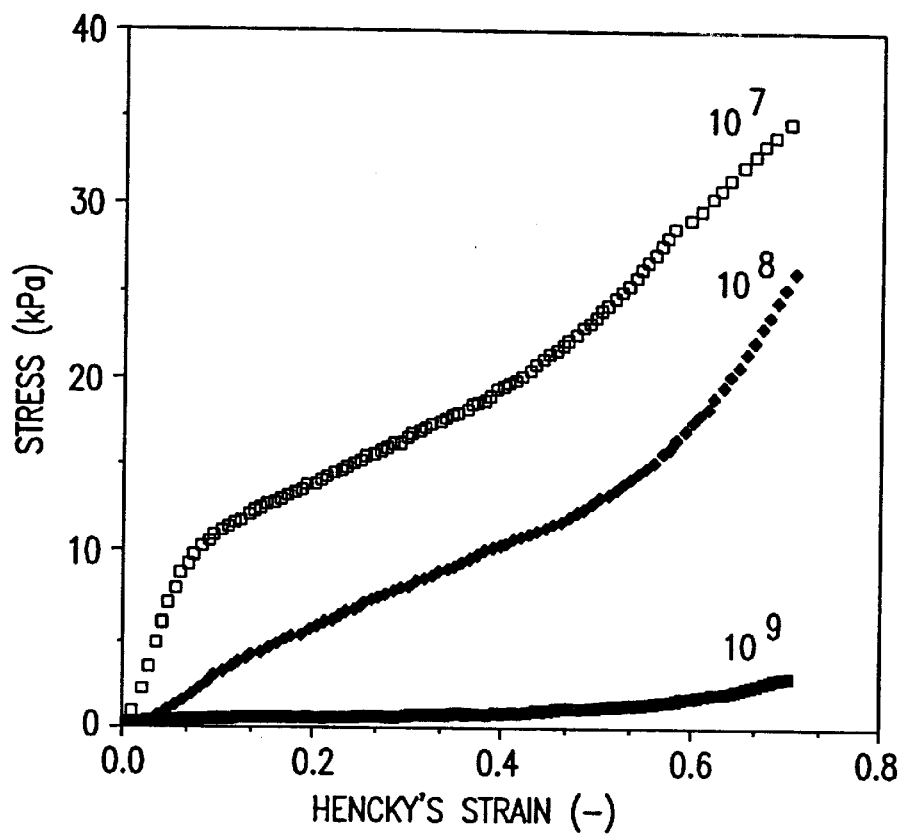
FIGS. 1 and 1A are graphs showing the stress-strain relationship of the "yeast" sponge after 3-days immersion in sucrose solution.

According to the invention the starting material for the production of sponges is one or more hydrocolloids, and there are produced air- or gas-filled structures of controlled parameters. It is an object of the invention to provide the food industry with a new carrier (matrix), which can be eaten nearly as is, as a low calorie food, or filled with fat or other high calorie constituents via infusion or other processes. Only a few modifications at the factory level, are therefore required for production of two totally different product types.

Specially designed sponges are produced for use in the diaper and hygienic pad industries. The sponges can be compressed to a smaller volume, while maintaining their absorbing capacity, and return to a larger volume only upon absorbing liquids. The big advantage of these sponges is their biodegradability. Decomposition is complete after a few months, generally about six months, thereby eliminating the problem posed by the currently used raw materials.

Biological sponges, such as those described here can also be used as filling materials in biochemistry, as well as carriers of enzymes and related substances.

DESCRIPTION OF THE PREFERRED EMBODIMENTS

Hydrocolloid sponges are dry gel products, the use of which can be economically feasible despite the high cost of the dehydration process. In principle, these sponges can be used as internal or external absorbants, after surgery or in burn treatments for example. Sponges were produced by preparing alginate gels which contained calcium carbonate, and allowing acid to diffuse into them resulting in gels that contained internally produced carbon-dioxide gas bubbles. Sponges were also produced by entrapping yeast within agar gels and immersing them in a sucrose solution for 3 and 7 days. Sponge properties were changed by including 0-40% oil within the gel before heat treatment and oil extraction. All gels were freeze-dried and kept over silica gel to avoid rehydration prior to testing and their mechanical properties were studied. The resultant cellular solids were compressed to ~80% deformation between parallel lubricated plates and the stress-strain relationships were fitted to a compressibility model previously developed for the sigmoid stress-strain relationships of cellular solids:

$\sigma = C_1 \epsilon / [(1+C_2\epsilon)(C_3-\epsilon)]$, where $\sigma$ and $\epsilon$ are the stress and strain, respectively, and $C_1$, $C_2$ and $C_3$ are constants. The sponges' inner structure was studied by scanning electron microscopy. Oil was found to change sponge structure and porosity, and yeast concentration also changed the sponges' characteristics.

The sponges' inner structure was studied by scanning electron microscopy. Oil was found to change sponge structure and porosity, and yeast concentration also changed the sponges' characteristics. Gels consisting of one hydrocolloid such as agar, carrageenan, gelatin, alginate, starch, pectin, gellan, kunjak mannan, two hydrocolloids such as xanthan gum plus locust bean gum, or three or more gelling agents were used, in most cases containing one or more further constituents. Hydrocolloid concentrations were up to about 5% (except in the case of gelatin which can be used in concentrations of up to about 20%). At a temperature above the gel's setting point air (or inert gases such as nitrogen and carbon dioxide) were incorporated by bubbling an air sparger. The hydrocolloid mixture contained 0-20% of a plasticizer such as glycerol. The resultant gel had 6000–8000 air bubbles per cubic centimeter. Before setting other ingredients such as up to 20%, sugar substitutes (up to 1%), salts (up to about 1%), colors at their respectively accepted levels, taste enhancers up to 1000 ppm and flavoring were added. The air filled gels were frozen by several techniques, including regular freezing, blast freezing and nitrogen freezing etc., and dried by techniques such as freeze dehydration, drying in a vacuum, or even regular drying when a low volume product was desired.

Gas-filled gels were alternatively produced by putting the above-mentioned food gels in a sealed chamber with liquid containing the same ingredients. Carbon dioxide, nitrogen land the like were then compressed into a chamber. The chamber was later opened abruptly causing the inclusion of air bubbles in the gel. Gas filled gels were dried as described above.

Another system, was designed to use nitrogen from a biological source. Yeasts were incorporated into gels containing the above mentioned ingredients. Gels were placed in sucrose, glucose, fructose or other sugar solutions. Sugar diffused into the gels, and carbon dioxide bubbles were formed and trapped within the gel matrix. Gas bubbles content was a function of yeast and sugar contents, temperature of diffusion, gel dimension, etc. Different gel textures were achieved by changing the percentage of yeast, $10^3$ to $10^9$ cells per gram, changing sugar type and content (0.2–30%) or changing temperature.

Gas filled gels were also produced by incorporating calcium carbonate (up to about 3%) and putting the gels in an acid solution (up to about 2.5%). After a short period of diffusion, gas was produced and trapped within the gel matrix. After freezing and drying as described above, sponge-like materials were obtained. Different gels were manufactured by changing the production order. First, regular gels (including plasticizer and other ingredients) were produced. Later acid was incorporated by diffusion and gels were put inside a calcium salt source. Carbonates diffusing into the gel were decomposed by the acid, producing a gas-filled gel.

A special gel, suitable for sponge production was produced by incorporating hydrocolloids inside the gel matrix. Agar, agarose, starch, pectin, alginate and the others at concentrations of up to about 3% can be supplemented to the above mentioned ingredients. Enzymes, such as an industrial blend of pectolytic materials were diffused into the gel to cut the pectin and to enable polymer fragments to diffuse out to the solution. Upon drying A sponge-like material had been produced. When agarose is incorporated into the initial gel, heating a water solution at 45° C. and the addition of sodium Iodide is necessary to decompose and diffuse out the agarose.

An emulsion composed of different percentages of oil in water (0–70%) was gelled using one or more of the above mentioned hydrocolloids. After gelation a slow heating process was applied, transforming the gel into a porous structure which produced sponge upon drying. In the following parts are by weight.

In another embodiment, the process for the production of a sponge comprising the following steps; i. expending a hydrocolloid gel with a gas, wherein the gas becomes entrapped as bubbles within the matrix of the gel and the gel remains unbroken, ii. drying of the gel, iii. incorporating of at least one fermenting microorganism to the gel, iv. contacting the gel with at least one fermenting microorganism, so as to form carbon dioxide and thereby to obtain the sponge.

The present invention demonstrates the usefulness of edible sponges as a carrier for vitamin A. They could serve as a good means of supplementation or fortification for young children. The magnitude of the positive impact of supplementation may not have been seen in all children because of the short duration of the present study. We assume that the longer the supplementation is maintained, the greater the opportunity for the children to restore their vitamin-A levels. As already noted VAD is strongly linked to blindness, in addition to presenting an increased risk of morbidity and death from gastrointestinal and respiratory diseases. An edible sponge, which fulfils the criteria of a viable micronotrient carrier, could solve these problems by facilitating the delivery of a logical solution to this problem. However, more studies are needed with a larger population to test the ability of the present carrier to include other micronutrients and vitamins, before a general recommendation can be made. Since such sponges are designed for human consumption, coloring, flavoring and other ingredients can be added (to the slurry before gelation) to improve their potential acceptance. The concept of hydrocolloid sponges is a new one. We believe these kinds of sponges will be used in the future not only as easily producible, affordable carriers for vitamins, but for other microelements as well, such as mineral and other food supplements.

EXAMPLE 1

An air-filled gel was prepared as follows:

| | |
|---|---|
| Sodium alginate | 2 |
| Calcium hydrogen orthophosphate | 1 |
| Calcium carbonate | 1 |
| Glucono delta-lactone | 1 |
| Citric acid | 2 |

Alginate powder 1% w/w, calcium hydrogen orthophosphate ($CaHPO_4$) 1% and 1% calcium carbonate were added slowly to stirred cold distilled water until complete dissolution of the ingredients. A freshly prepared solution of 1% glucono-delta-lactone was then admixed with this solution using vigorous stirring. The alginate solution was poured into a plastic container (10×10×8 cm) and let to set there. After 48 hours specimens were taken from the slab using a cork borer and immersed in citric acid solution 2%. The volume of the citric acid solution was about 100 times the volume of a single gel specimen to guarantee excess acid.

With the diffusion of the citric acid solution there were formed carbon dioxide bubbles, part of which were entrapped in the gel. There resulted a gel containing about 6,500 bubbles per cubic centimeter and the gel was trasferred to cold storage at −20° C. and afterwards to drying while frozen, at −50° C. and at 40 mm pressure. There was obtained an edible sponge, devoid of any caloric value. It is possible to introduce into the acid solution a small concentration of a sweetening agent, such as 0.5% or less saccharin or food color (10 ppm tetrazine) so as to obtain as final product a sweet tasting yellow colored calorie less edible sponge.

EXAMPLE 2

A sponge was prepared as in Example 1, but which has nutritional value. The citric acid solution used contained 12% sucrose and 25 ppm red color (Ponceau 4). After about 3 hours the gel was frozen in a blast freezer during about 2 hours, and lyophilized at −45° C. at 30 mm pressure.

There was obtained a sponge having a density of about 0.07 g/cm³ and a caloric value of about 0.5 cal/gram.

EXAMPLE 3

| | |
|---|---|
| Agar | 1 |
| Pectin | 1 |
| Water | 98 |

The agar was dispersed in water and after 10 minutes stirring, the solution was heated to 95° C. for 2 minutes and cooled down to 70° C. At this stage the pectin was slowly introduced into the solution, and after cooling there was obtained an agar-pectin gel. This was cut up into desired size and introduced into a 1,000 ppm solution of pectolytic enzymes (commercially available). This constitutes a large excess of such enzymes respective the gel. The system was warmed to 38° C. and maintained at this temperature during 5 hours. The excess of the enzyme was removed by immersion in water at 38° C. during half an hour, and this was repeated 3 times. The gel was frozen in liquid nitrogen and freeze dried. There was obtained a product of a density of from about 0.03 to about 0.1 g/cm³.

EXAMPLE 4

| | |
|---|---|
| κ-Carrageenan | 1.5 |
| Konjak mannan | 1.5 |
| Potassium chloride | 20 |
| Soya oil | 20 |
| Water | 76 |

The konjak mannan (a type of hydrocolloid) was dispersed and dissolved in the water which contained 1% potassium chloride. After warming to 70 degrees C., κ-carrageenan was added and the solution was stirred until this dissolved. After cooling to 45 degrees C., and in any case to above the setting point of the κ-carrageenan. Then soya oil was added with vigorous stirring to homogenization and the resulting suspension was cooled rapidly to room temperature. This prevents separation of the oil. The gel, containing the oil, was left under refrigeration for 24 hours and introduced into water at 35° C. under vigorous stirring. Thus part of the oil is separated, and the remaining gel was frozen and freeze dried. There was obtained a spongy edible product, density: 0.075 g/cm³, edible value: about 0.8 cal/g.

Example 5

There was prepared a 2% solution of gellan, and 0.2%, calcium chloride (or 2% agar without such additive) or 2% carrageenan with 1% of potassium chloride, or of 1% xanthan and 1% locust bean gum). The gellan solution was prepared by gradually adding gellan powder to an aqueous solution of the calcium chloride at about 90° C. The solution of gellan was cooled to about 40° C. or less, so as to bring about gelification. At this stage there was added to one liter of the solution a suspension of 10 of baking yeast of the saccharomyces type, and the solution is cooled rapidly to obtain gelification. In order to avoid a drastic reduction of the active yeast cells one has to work with a hydrocolloid which sets at room temperature. The obtained gels were cut into circular disks of about 20 mm diameter and 20 mm height, and inserted into a 10% sucrose solution. The sucrose diffuses into the gel and the yeast ferments the sugar resulting in carbon dioxide bubbles which are entrapped in the gel (about 10,000 bubbles per cubic centimeter). The gel containing the carbon dioxide, which contains also residual sugar and ethanol produced during the fermentation, is frozen and dried, resulting in an edible sponge of unique structure.

It is possible to carry out such processes with beads of the gel and thus obtain spongeous products for use in biotechnology.

EXAMPLE 6

A run was carried out with a solution of 2% into which there was introduced a gas such as oxygen, carbon dioxide, nitrogen or air, and after gelation, cutting up to desired shapes, these are subjected to freeze drying, as in preceding Examples.

EXAMPLE 7

Gels produced according to Example 5 or 6 can be inserted into a pressure vessel, and after equilibration, the pressure is suddenly released, resulting in incorporation of air bubbles. After freezing and drying a sponge is obtained.

EXAMPLE 8

Creating Sponges by an Immobilization Process:

*Saccharomyces cerevisiae* (yeast) was cultivated in Potato Dextrose Agar broth (Difco, Detroit, Mich., USA) for 2 days at 30° C. The cells were harvested by centrifugation at 3000 g for 15 min at 5° C. and washed twice with sterile deionized water. The yeasts were diluted as needed in sterile deionized water and stirred at 5° C. no more than 15 min until immobilization was performed. Yeasts were counted directly in a Neubauer chamber (West Germany). Immobilization was performed by thoroughly mixing, nine parts 2% (w/w) agar with one part diluted yeast solution to obtain gels with $10^8$ and $10^9$ immobilized yeast per ml. The microorganism suspension was added directly after bringing the cell suspension to 28° C. The gel-cell mixture was mixed for 5 min prior to pouring into stainless-steel cylindrical molds. Reference gels with no microorganisms were prepared in parallel. The gels were immersed in a 5% sugar solution, to induce fermentation. The volume of the sucrose solution was ~30 times that of the immersed gels. The mechanical properties of gels with entrapped carbon-dioxide bubbles were studied after 3 and 7 days. Parallel gels were freeze-dried and checked for their sponge properties and structure.

EXAMPLE 9

Mechanical Properties of Gels

Gels were compressed to failure between parallel lubricated plates at a constant deformation (displacement) rate of 10 mm/min, corresponding to an initial $0.011s^{-1}$ strain rate using an Instron Universal Testing Machine model 1100. The Instron was connected to an IBM-compatible personal computer by an analog to digital conversion interface card. A program developed at the Instron Corporation (Canton, Mass.) and modified in our laboratory, performed the data acquisition and conversion of the Instron's continuous voltage vs. time output into digitized force-deformation, force-time, stress-strain, or stress-time relationships with any desired definition of stress and strain. All mechanical tests were performed in triplicate, with samples taken from two separate batches.

EXAMPLE 10

Mechanical Properties and Porosity of Sponges

The different sponges—those with internally produced gas bubbles, those produced by fermentation and those including oil within the gum mixture, were freeze-dried to create the cellular solid structures. They were compressed to 80% deformation between parallel lubricated plates at a constant deformation (displacement) rate of 10 mm/min, using the Instron. The Instron's continuous voltage vs. time output was converted into stress vs. Hencky's (natural) strain relationships:

$$\epsilon = \ln [H_0/(H_0-\Delta H)] \quad (1)$$

and $$\epsilon_H = \ln [H_0/(H_0-\Delta H)] \quad (2)$$

where $\sigma$ and $\epsilon$ are stress and Hencky's strain, respectively, F is the momentary force, $\Delta H = H_0 - H(t)$ is the momentary deformation, $A_0$ and $H_0$ are the original specimen's cross sectional area and height, respectively, and $H(t)$ is the height at time t. Since the cross-sectional area of a compressed solid sponge specimen rarely expands to any significant extent (Gibson and Ashby, 1988), the engineering and "true" stresses could be treated as equal for all practical purposes (Swyngedau et al., 1991).

The individual relationships were fitted to a compressibility model previously developed for the sigmoid stress-strain relationships of cellular. solids (Swyngedau et al., 1991a; Nussinovitch et al., 1989; Swyngedau et al., 1991b):

$$\sigma = C_1 \epsilon / [(1+C_2 \epsilon)(C_3-\epsilon)] \quad (3)$$

where $\sigma$ and $\epsilon$ are the stress and strain, respectively, and $C_1$, $C_2$ and $C_3$ are constants calculated by nonlinear regression of the Systat package. The constant $C_1$ is primarily a scale factor and has stress units. The constant $C_2$, dimensionless, is a measure of the shoulder's prominence in the stress-strain curve-that is, when $C_2=0$, the relationship has no shoulder and its slope increases monotonically. The constant $C_3$, also dimensionless, is a rough measure of the steepness of the stress-strain curve in the high-strain region. According to equation 3, when $\epsilon$ goes to $C_3$, $\sigma$ tends to infinity. $C_3$ is determined largely by the strain level at which collapse of the open structure has been completed and most of the resistance to deformation has been shifted to the compacted solid cell wall material. All mechanical tests were performed in duplicate.

Porosity was defined as the volume fraction not occupied by particles or solid material and could therefore be expressed as:

Total porosity=1−(bulk density/solid density) (Peleg and Bagley, 1982).

EXAMPLE 11

Scanning Electron Microscopy

SEM micrographs were obtained by the following procedure. A new double-edged razor blade was used to cut through the solid foams and expose the Internal surface features. Single downward cuts were used to produce 1- to 2-mm thick slices of samples. A 1:1 mixture of colloidal graphite in isopropyl alcohol and Duco household cement was used as a conductive mounting adhesive. Sample pieces were mounted onto 10×10 mm, aluminum SEM stubs. Samples were coated in a Polaron E5100 sputter-coating unit with a Peltier cooling stage. Samples were coated with approximately 50 nm of Au/Pd (60:40 w/w), and examined in a Jeol JSM 25S scanning electron microscope at an accelerating voltage of 15 kV and a working distance of 48 mm.

Figure 1A:
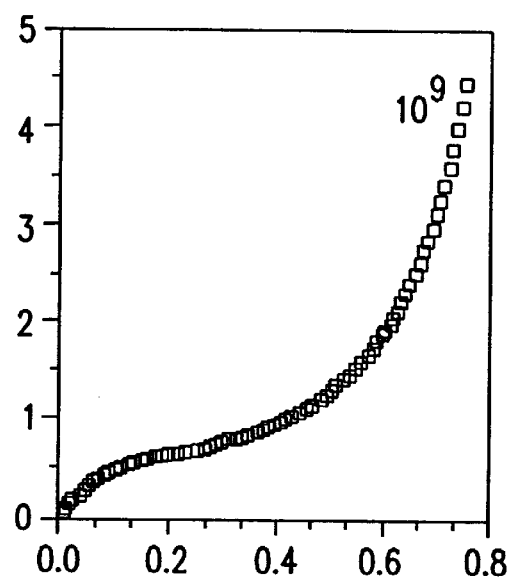
Figure 2:
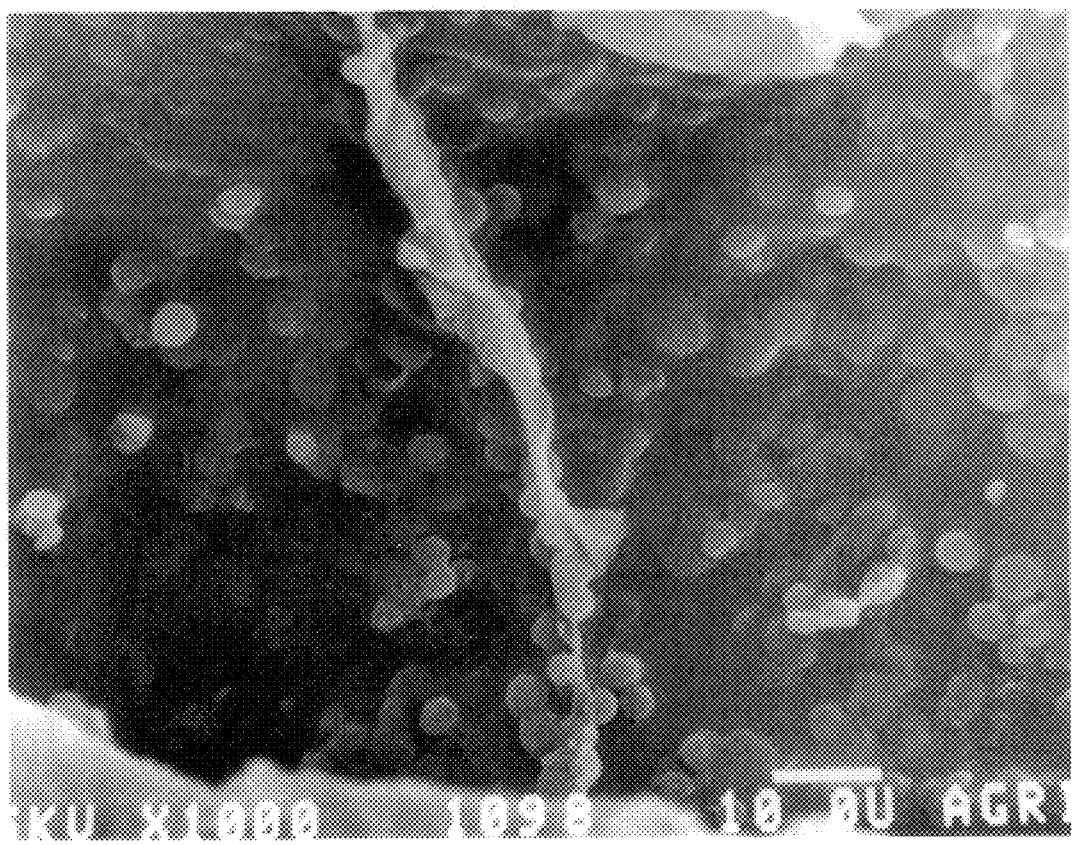
FIG. 2 is a representative of the structure of a sponge having yeast cells distributed in and on the cell walls.
Figure 3:
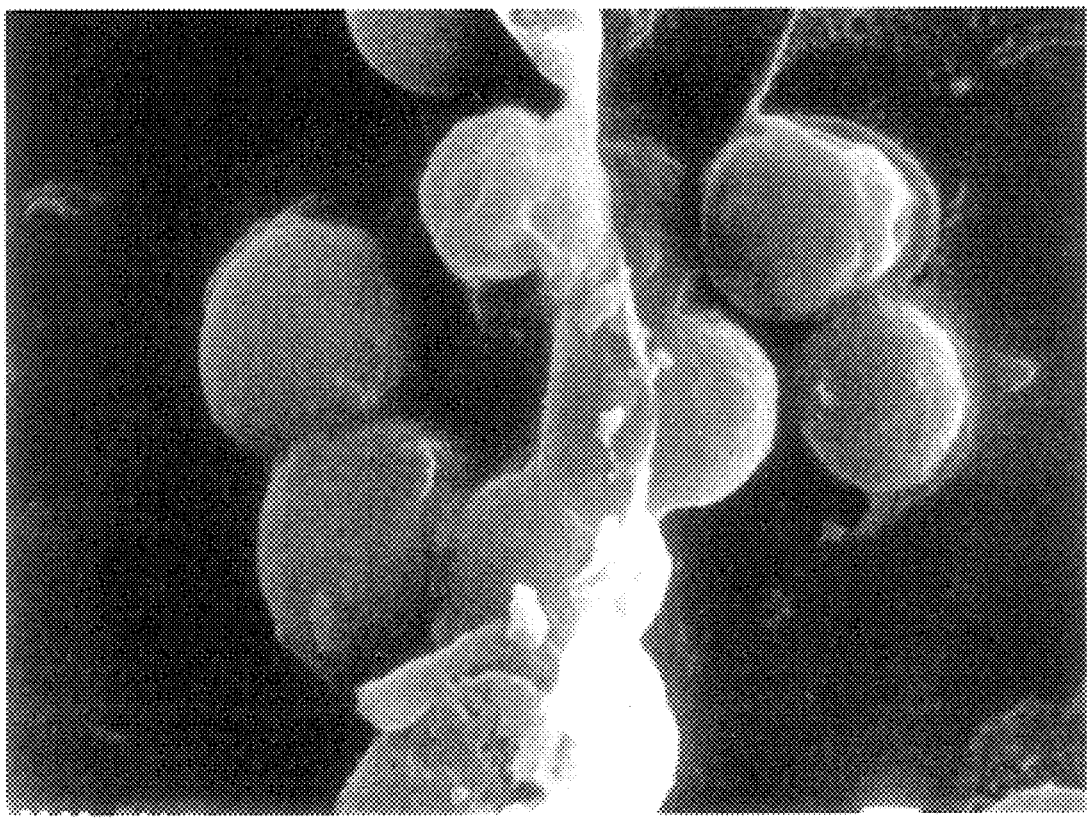
FIG. 3 is an enlarged detail of part of FIG. 2.

The influence of yeast immobilization on the mechanical properties of an agar gel at time zero, 3 days and 7 days is presented in Table 1. It was found that the higher the concentration of the microorganisms within the gel, the higher the disturbance to its integrity. In other words, stresses at failure and deformability moduli decreased after the immobilization of the yeasts. The brittleness of the gels also increased (their strain at failure decreased). Similar results have been achieved previously for bacteria, yeast and spore immobilization (Nussinovitch et al.,1994). After yeast immobilization the gels were immersed in an excess volume of 5% sucrose solution (the sucrose content in the gels reached the 5% level after ~5 h at 30° C.). Slow fermentation occurred, perhaps because no nitrogen source was added. It is also possible that the lag time for yeast growth was longer causing immobilized yeast to react later than their non-entrapped counter parts. As a result of the fermentation, carbon-dioxide bubbles and ethanol were produced and a decline in pH was observed. The gas bubbles moved from their site of production (throughout the inside of the gel) to the surface of the gel, causing some mini-cracks in the gel and later influencing the structure of the resultant sponge. The longer the fermentation, the less strong and stiff the gels (Table 1). The shape of the stress-strain relationship of the "yeast" sponge after 3 days immersion in sucrose solution is shown in FIG. 1 and FIG. 1A. All sponges showed the sigmoid curve characteristic of cellular solids, which is a manifestation of the three deformation mechanisms mentioned previously. The constants in equation 3 for the description of the stress-strain relationship, achieved by nonlinear regression, are presented in Table 2. The major difference between sponges was in the magnitude of $C_2$. The higher the concentration of the entrapped microorganisms, the smaller the value of this constant, which reflects shoulder shape and prominence in the stress-strain curves. Small mean square error (MSE) values indicated a good fit. The structure of these sponges is presented in FIG. 2. The yeast cells seem to be distributed in and on the cell walls of the sponge and to be attached to its outer surfaces. As previously mentioned, the compression of all sponges produced after 3 days of gel immersion in sucrose solution resulted in stress-strain relationships similar to those of a regular sponge. This was true for all yeast concentrations used in this study. However, after 7 days immersion in the sucrose solution, a different phenomenon was observed. For $10^7$ yeasts/g gel a "regular" stress-strain relationship was still observed, whereas higher initial yeast concentrations such as $10^8$ and $10^9$ yeast/g gel, materials were produced which did not resemble sponges in their stress-strain behavior. This can be partially explained by noting that an increase in the time of fermentation results in an increase in biomass (a fivefold increase in the protein content of gels before freeze-dehydration performed was observed). From FIG. 3 depicting a magnified portion of FIG. 2, it can be concluded that in compressed sponges with initially high yeast concentrations after 7 days immersion in sucrose solution, compaction of a "yeast-hydrocolloid" rather than a hydrocolloid network occurs, resulting in different products and properties. Comparing sponges prepared from gels without yeast to those prepared from gels with $10^9$ entrapped yeast/g (after 3 days gel immersion in a 5% sucrose solution), is performed, a decrease in porosity from ~96% to ~92% was observed. This may be due to the increased dry matter content of the sponge.

EXAMPLE 12

Into an agar solution there was introduced a quantity of about 20 Weight-% of an oil, all other constituents being as in the preceding example and this was processed as before. The product has a reduced porosity of about 80%. This demonstrates another option for the control of the porosity of the product. The wall of the cells formed are more rounded and the sponge is less breakable.

EXAMPLE 13

Bacteria of the kind of P. stutzeri were immobilized in a chitosan-alginate gel. In addition to the gas formation by fermentation, a polysaccharide was produced by the microorganisms, which enhances the mechanical properties of the sponge before drying and prevents its disintegration.

TABLE 1

Influence of time of sucrose fermentation with different concentrations of entrapped Saccharomyces cerevisiae on the mechanical properties of 2% agar gels

| | Fermentation time at 30° C. | | | | | | | | |
|---|---|---|---|---|---|---|---|---|---|
| | 0 days | | | 3 days | | | 7 days | | |
| Yeast concentration (CFU/g) | Stress at failure (kPa) | Strain at failure (−) | ED (kPa) | Stress at failure (kPa) | Strain at failure (−) | ED (kPa) | Stress at failure (kPa) | Strain at failure (−) | ED (kPa) |
| 0 | 39.5 ± 1.1 | 0.26 ± 0.01 | 136.7 ± 4.1 | 24.8 ± 1.2 | 0.23 ± 0.01 | 122.2 ± 2.2 | 22.4 ± 1.0 | 0.22 ± 0.01 | 119.2 ± 2.4 |
| $10^8$ | 28.9 ± 1.2 | 0.25 ± 0.02 | 134.9 ± 2.8 | 22.7 ± 0.8 | 0.23 ± 0.02 | 111.4 ± 1.8 | 20.4 ± 0.8 | 0.21 ± 0.01 | 101.8 ± 2.0 |
| $10^9$ | 22.2 ± 1.4 | 0.21 ± 0.01 | 129.7 ± 2.2 | 11.5 ± 0.5 | 0.19 ± 0.01 | 59.9 ± 1.0 | 9.4 ± 0.6 | 0.17 ± 0.01 | 44.4 ± 0.6 |

Each result is the average of at least six determination ± SD taken from two separate gel batches.

TABLE 2

MODEL CONSTANTS OF NONLINEAR REGRESSION IN COMPRESSION STRESS-STRAIN RELATIONSHIPS OF YEAST-GELS AFTER 3 DAYS OF FERMENTATION IN FREEZE-DRIED SPONGES

| CFU/g | $C_1$ (Mpa × $10^{-2}$) | $C_2$ (−) | $C_3$ (−) | MSE[a] (× $10^{-7}$) |
|---|---|---|---|---|
| $10^7$ | 31.7 | 19.1 | 1.13 | 2.16 |
| $10^8$ | 4.4 | 4.7 | 0.98 | 0.74 |
| $10^9$ | 0.4 | 7.8 | 0.96 | 0.02 |

[a]MSE mean square error.
CFU—colony forming units.

EXAMPLE 14
Gum-oil Gels and Sponges

Alginate gels were produced as above, except that soya oil was added by homogenization (APV Rannie, model mini lab type 8.30H) to 40% (w/w) into the gum solution to which a 2%(w/w) GDL solution was later added. Tween 80 (0.1%, w/w) was also included in the oil before homogenization. Gels were kept at 5° C. for 24 h. They were then equilibrated to room temperature before heat treatment, 5 min/15 min in warm water (85° C.), to induce the oil's removal from the gels into the warm water in which they were immersed. The volume of the warm water was about 20 times that of the gels. The water was replaced three times, and the oil-alginate gels were therefore kept immersed for about 45 min, before they were compressed as gels or freeze-dried and compressed as sponges, as described further on.

EXAMPLE 15

Figure 4:
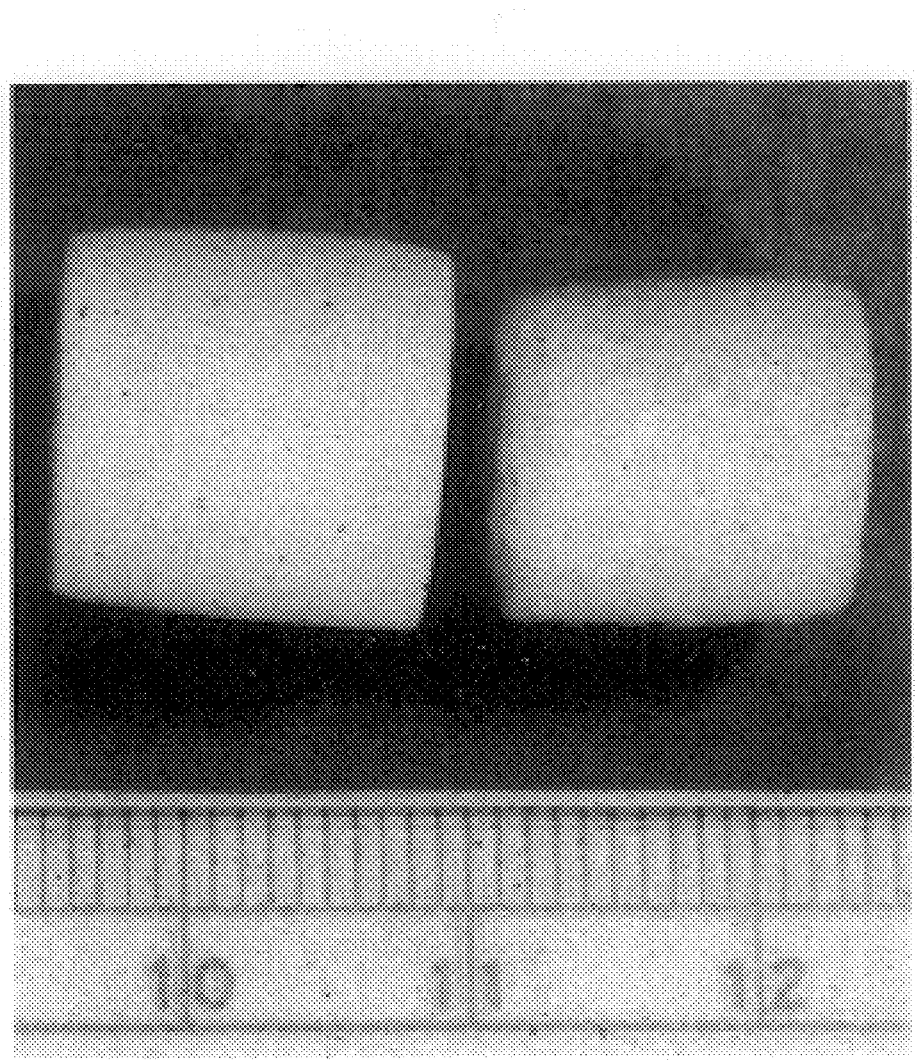
FIG. 4 shows the appearance of a $CO_2$-filled alginate gel. Left-gel with carbonate before acid diffusion. Right-alginate gel after acid diffusion. Note bubbles bulging from its outer surface.

Sponges Created by Drying Gels Filled with Internally Produced Carbon-dioxide Gas Bubbles FIG. 4 shows a $CO_2$-filled alginate gel, before (left) and after (right) completion of the process, i.e. before and after the acid had diffused to the center of the gel. Gas bubbles seem to be trapped within the gel body and to bulge from its outer surface. The motion of the acid within the gel was by controlled diffusion, as evidenced from the linearity of the penetrated distance vs. $t^{1/2}$. As previously mentioned, the gels used in these experiments contained phenolphthalein in them so that the distance could be measured directly with a caliper after the specimen was dissected. The slope of the distance vs. $t^{1/2}$ slope was about 0.7 mm×min$^{-0.5}$.

Inside the alginate gels, small gas bubbles were created. After 2.5 h, about 900 bubbles/cm$^3$ were counted. This number increased to about 2000–2700 after 24 or 36 h, depending on the carbonate concentration. Bubble formation decreased the density of the gels, causing them to float. After a while bubbles began travelling out of the gel, causing some damage to its integrity, and allowing liquid to gradually fill the empty space. Consequently, the gels began to sink again.

Figure 5:
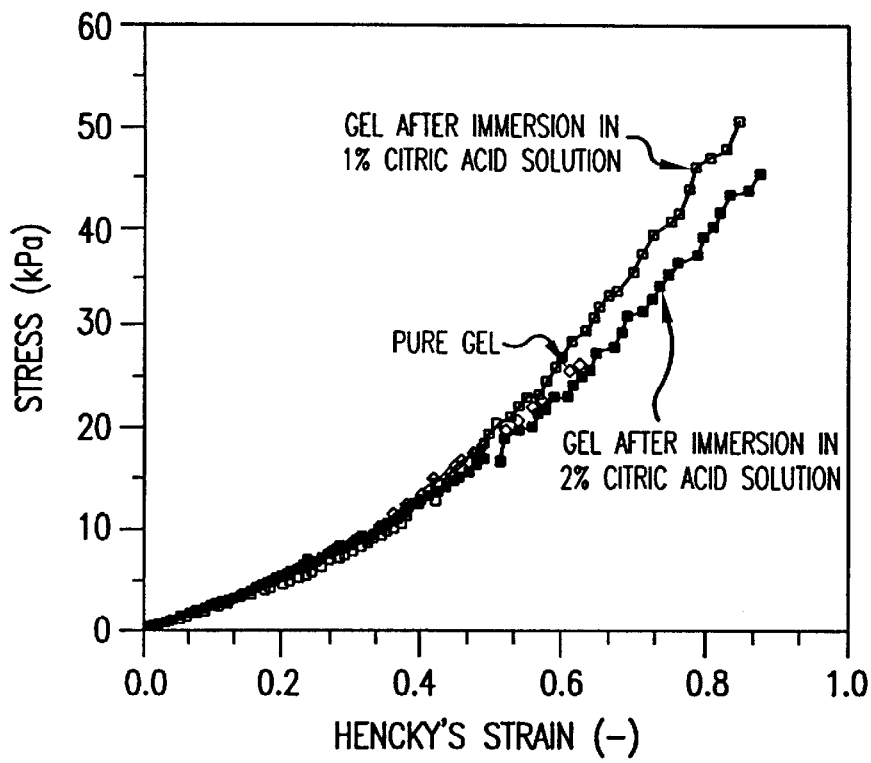
FIG. 5 shows Stress-strain relationships of alginate gels before and after acid diffusion.
Figure 6:
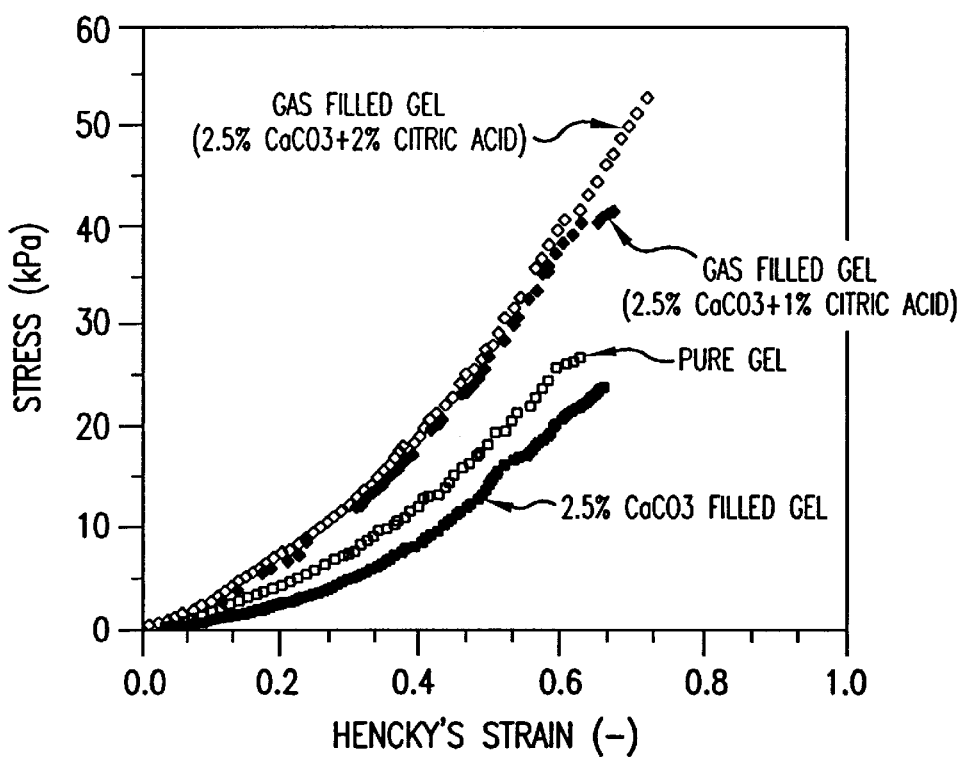
FIG. 6 shows Stress-strain relationships of untreated alginate gel, and of alginate gels with 2.5% added carbonate, before and after 1 and 2% citric acid diffusion.

Typical stress-strain relationships of ordinary and gas-filled alginate gels are shown in FIGS. 5 and 6. Immersion in acid increased gel strength and deformability. For example, alginate gels without carbonate immersed for 2.5 h in a 0.5% citric acid solution increased their average stress at failure from 28 to 46 kPa. The Hencky's strain of these gels increased from 0.64 to 0.83, indicating that the gels become less brittle. The increase in failure stress and strain was found for all tested alginate systems, immersed in 0.5–2.0% citric acid solutions. This may be due to acid-induced cross-linking, which helped the gel retain its mechanical strength, even in the face of the structural disruption caused by bubble formation. The presence of carbonate, however, had a disruptive effect, primarily manifested in lower stiffness. Thus gel strength depended on both acid and calcium carbonate concentrations.

Figure 7:
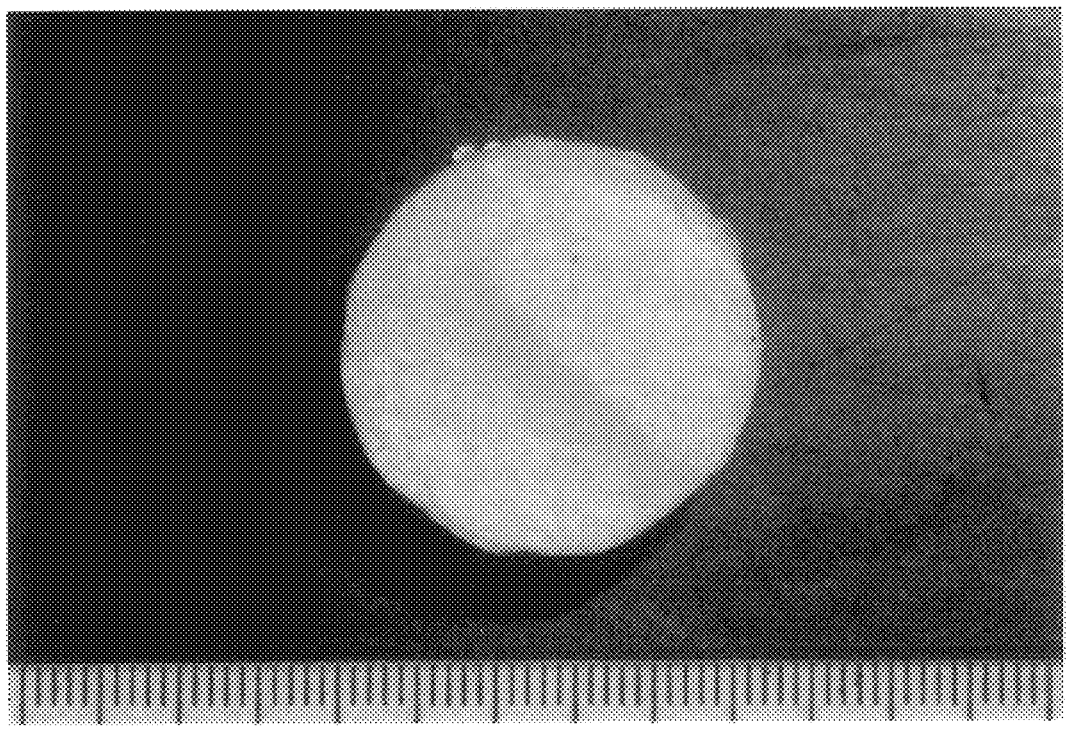
FIG. 7 is the typical appearance of freeze-dried gel specimens.
Figure 8:
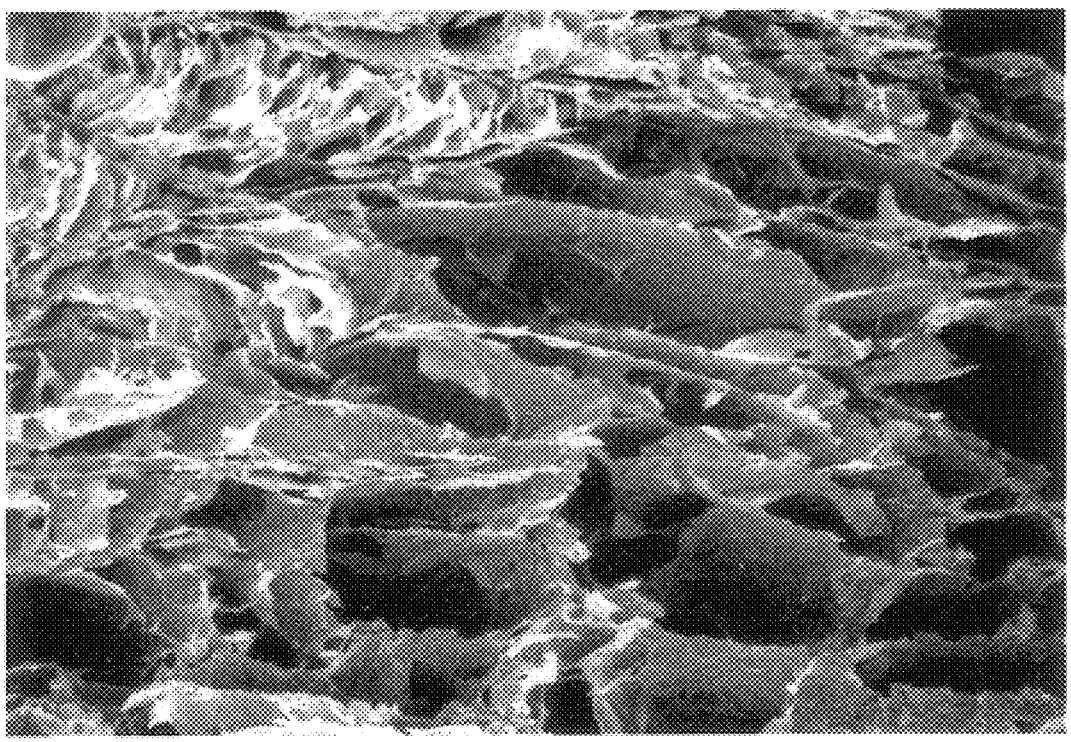
FIG. 8 is the cellular structure of a 1% alginate sponge.
Figure 9A:
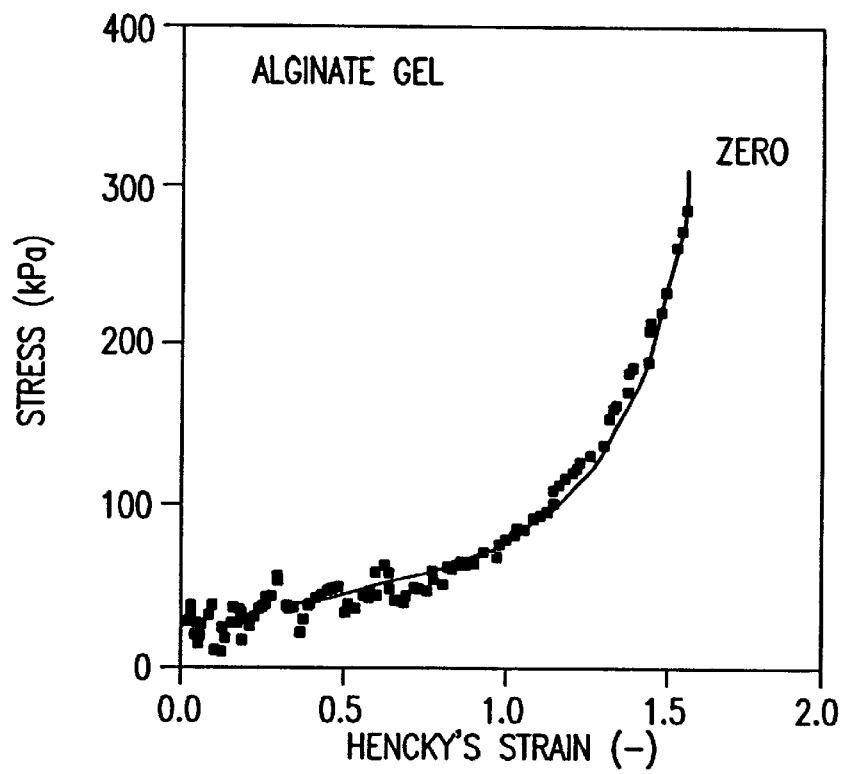
FIGS. 9A and 9B show typical stress-strain relationships of the alginate sponges resulting from gels without treatment and after 1.8 h immersion in citric acid solution. The solid lines are the fits of eq #3.
Figure 9B:
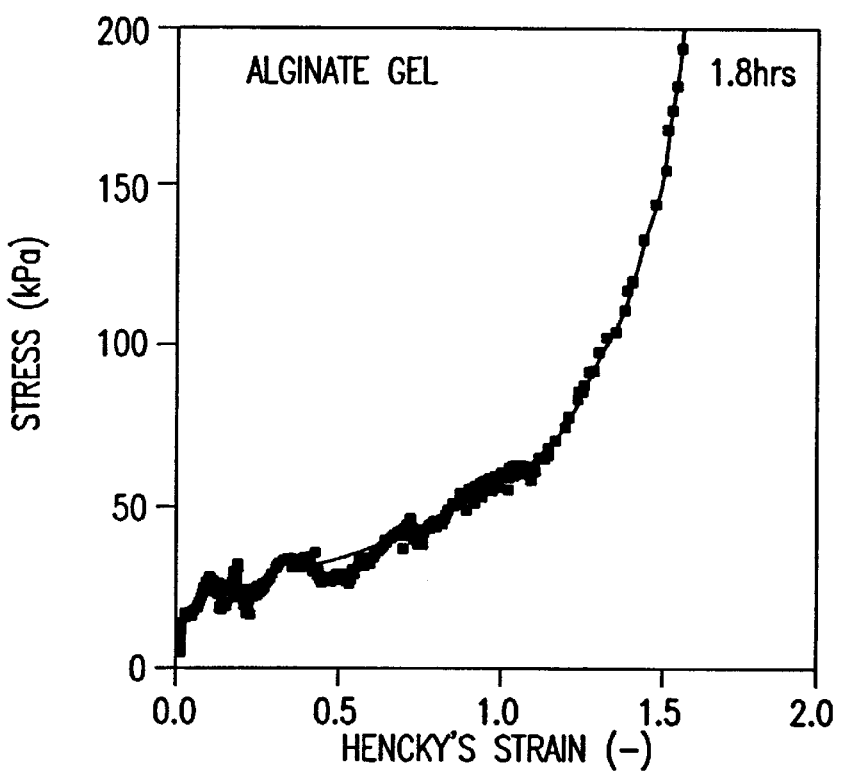

Freeze-dried gel specimens are shown in FIG. 7 and their cellular structure in FIG. 8. Since the shape of the dried specimen (final product), approximates that of the gels before dehydration, products can be designed in any shape or size, by building the desired molds. The structure of the cellular solid is determined by the freeze-dehydration process as well as by changes in the gel's processing and components. Typical stress-strain relationships of the dry sponges are shown in FIGS. 9 and 9A. They all showed the sigmoid shape characteristic of cellular solids, which is a manifestation of three deformation mechanisms. The first part of the curve, i.e., the almost instant rise of the stress, represents the deformation of the intact sponge. Since all the tested specimens were brittle, failure occurred after a very small, hardly measurable strain. The moderate slope of the curve represents progressive rupture and collapse of the cell walls and densification of the compressed specimen. This was followed by compression of the compacted cell wall solid material, which is manifested in the rapid rise of the slope of the stress-strain curve. The stress-strain curves of the alginate sponges, especially in the second region, were irregular. Such irregular relationships are quite common in brittle solid foams (Attenburrow et al., 1989). The fit of equation 3, which was originally developed for spongy baked goods and polymeric sponges and is shown as a solid line in FIGS. 9 and 9A, indicates that the compressibility model suits the type of sponge created here. The regression parameters of equation 3 are summarized in Table 3. The magnitude of the mean square error for the alginate sponges is a reflection of the inherent ruggedness of the stress-strain relationships rather than a reflection of the fit of equation 3 as a model. With the alginate sponges, immersing of the gels in an acid bath did not result in a drastic loss of mechanical integrity. This appears to be because the disruptive effects of the bubble formation were at least somewhat offset by the more extensive cross-linking. The constants $C_1$, $C_2$ and $C_3$, as previously mentioned, were determined by a nonlinear regression procedure that is based on minimizing the mean of the squared deviations.

EXAMPLE 17

Oil Gels and Sponges

Oil was included in the sponges to change properties such as structure, density, porosity, etc. The properties of the oil, as provided by its local manufacturer, are presented in Table 4. The mechanical properties of alginate-oil gels are shown in Table 5. The higher the content of the oil within the gel, the lower its stress at failure, and stiffness as reflected by the deformability modulus. The higher the content of the oil, the smaller the Hencky's strain at failure, or in other words the gel was more brittle. Two systems of oil gels and sponges were dealt with in this study: in the first gels with and without oil were simply freeze-dried directly; In the second, the gels were heat-treated at 85° C. for 15 min in water, three times in succession. Each time the water and the extracted oil were discarded. Oil content in the gels, and sponges was estimated by the Soxhlet method and is given in Table 6. After heat treatment, 40–50% of the oil had "left" the gel. After freeze-dehydration the oil percentage within the sponge increased.

Figure 10:
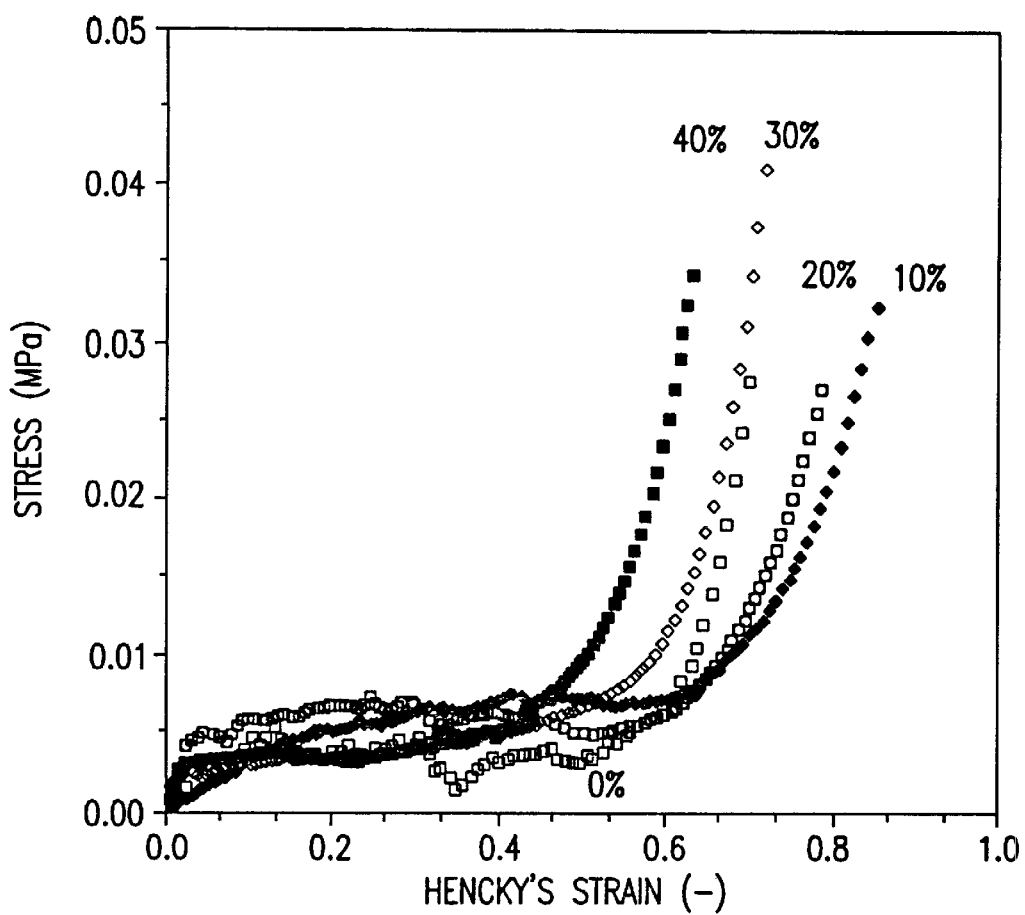
FIGS. 10 and 10A show Stress-strain relationships of oil sponges from untreated gels. Initial oil concentrations (0–40%) are as mentioned on the figure. The solid lines are the fit of eq #3.
Figure 10A:
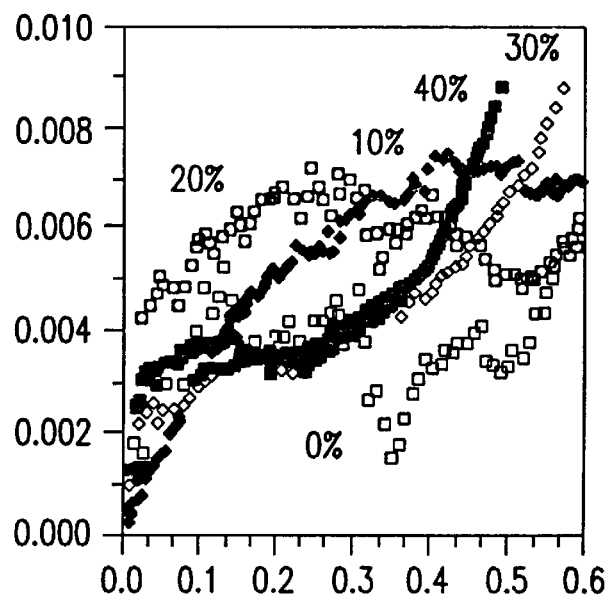
Figure 11:
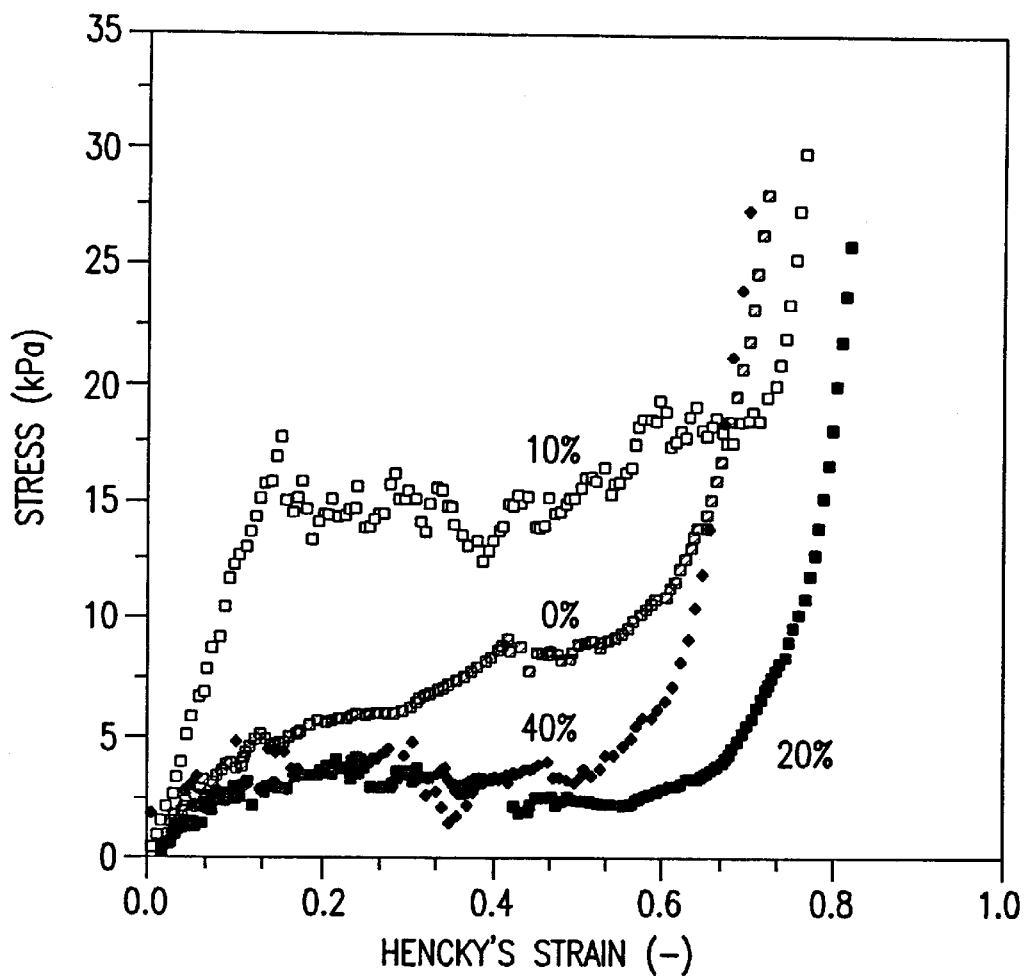
FIG. 11 is Stress-strain relationships of oil sponges from heat-treated gels.
Figure 12:
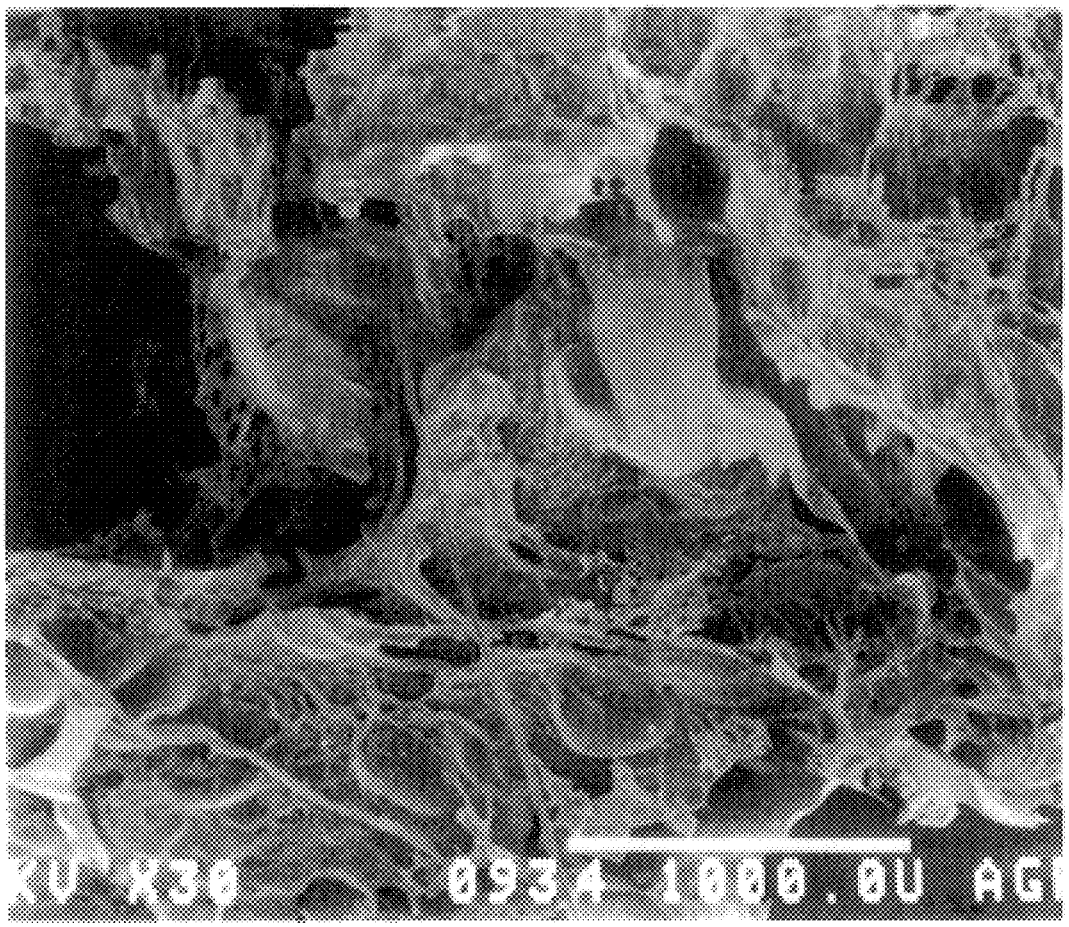
FIG. 12 is Agar sponge structure. No oil included.
Figure 13:
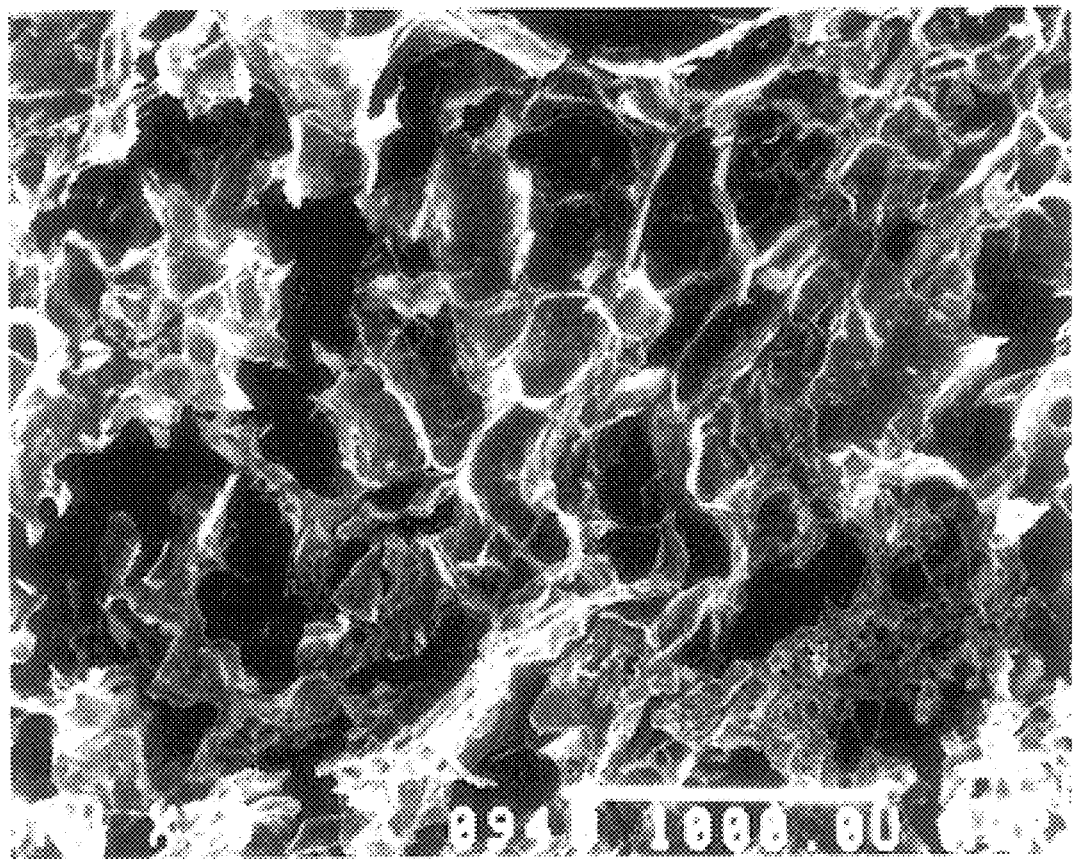
FIG. 13 is Agar sponge with 10% oil (compare with FIG. 12 to note the differences)
Figure 14:
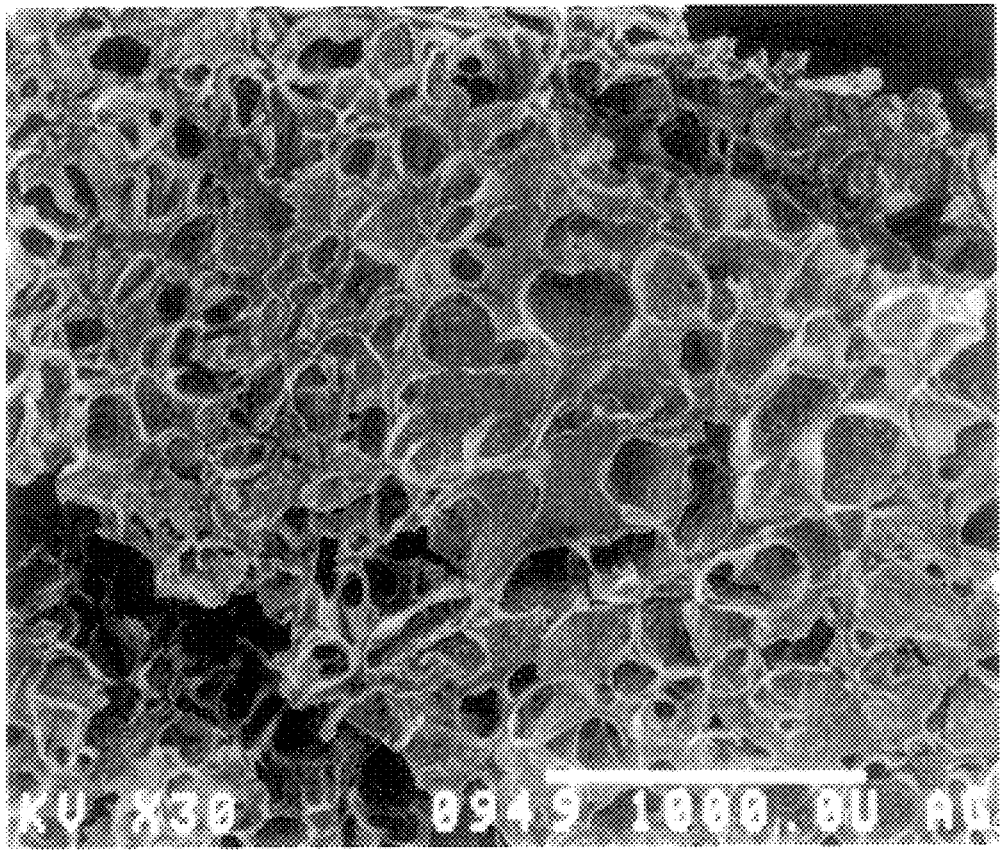
FIG. 14 is Agar sponge with 30% oil (compare with FIGS. 12 and 13: to note how the structure changes and the cells begin to close up)
Figure 15:
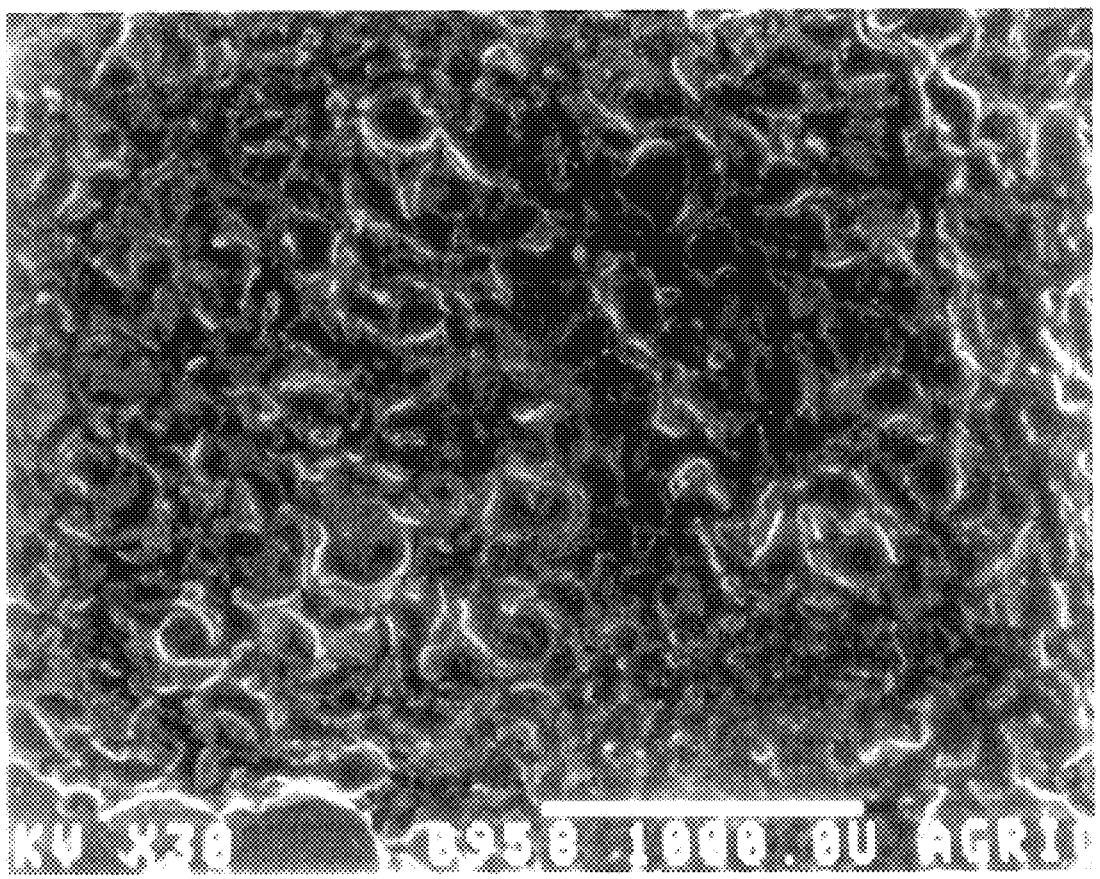
FIG. 15 is Agar sponges with 40% oil (compare with FIGS. 12 to 14: to note how the total structure of the sponge has changed, becoming smoother)
Figure 16:
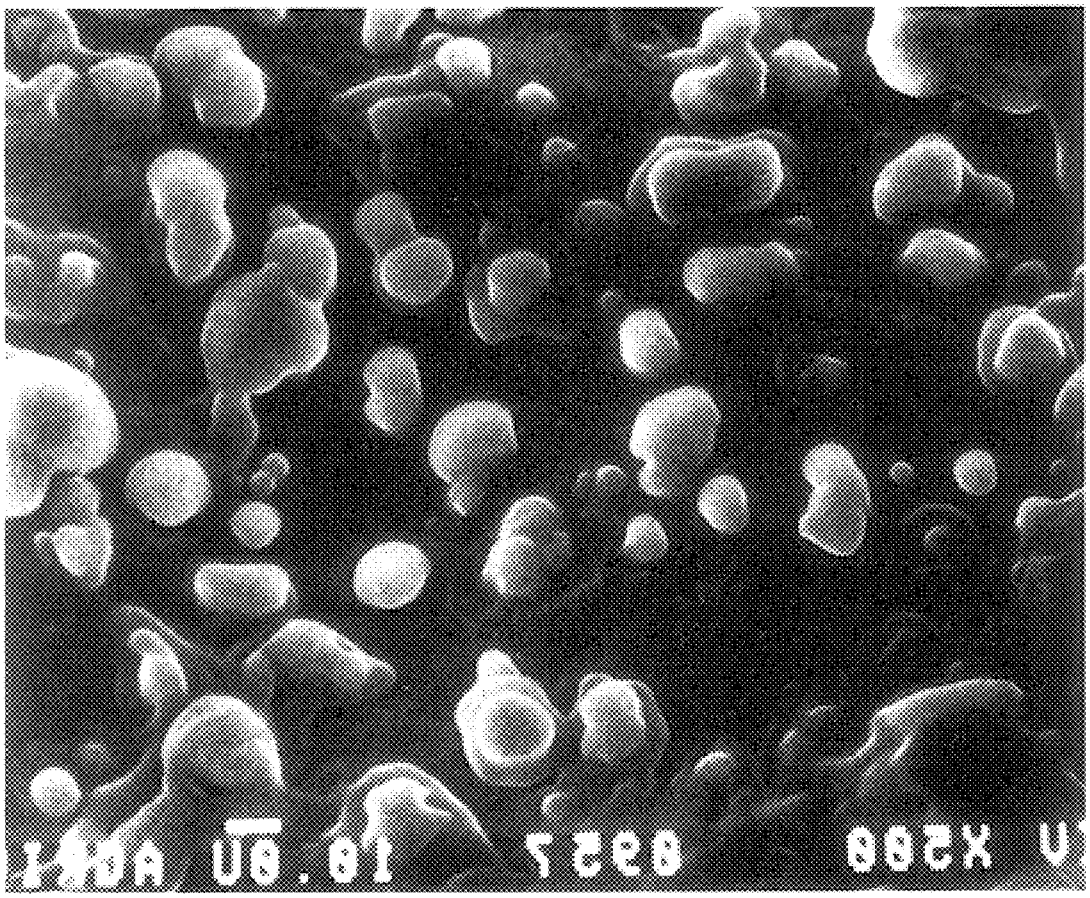
FIG. 16 is SEM micrograph of an agar-oil sponge. The oil is presented as mini-drops embedded within the solid wall of the matrix.

The stress-strain relationships of the oil sponges are presented in FIGS. 10 (as is) and 11 (after heat treatment and partial oil extraction), and the results of the nonlinear regression for determining the constants of equation 3 for the curves in FIG. 9 are presented in Table 7 . In FIGS. 10 and 10A the ruggedness of the curves up to 40% deformation is shown. Two facts can be observed. The higher the oil content within the sponge, the smoother, the curve, in addition the $C_2$ constant of the nonlinear regression decreases. The higher the bulk density of the sponge (from 0.074 g/cm$^3$ for those without oil inclusion to 0.29 g/cm$^3$ for 40% initial oil inclusion before freeze-dehydration), the more the stress tends to steepness at smaller deformations. Heat treatment was used as one of the possible methods of oil extraction. After extraction (and see FIG. 11 and the above discussion), the stress-strain curves became more rugged. The heat treatment may disrupt the gel structure, physically damaging the specimen surface. The porosity of the sponges changed dramatically after oil inclusion. When the oil was left the gel, porosities changed from ~95% (no oil included) to ~80% (40% oil included in the gel before freeze dehydration). The porosity of the other non-heat-treated system was not studied. Electron microscopy of the sponges (FIGS. 12–15) revealed that the higher the oil content in the sponge, the more closed cells within its structure. In addition, the structure of the cells changed from big openings to rounder, smaller ones. The oil can be seen as mini-drops embedded within the solid wall of the matrix (FIG. 16).

EXAMPLE 16

Hydrocolloid sponges are in essence dry-gel products. They were produced by preparing cold-set 1% alginate gels containing vitamin A. All gels were freeze-dried and kept over silica gel to avoid rehydration prior to testing, or were packages in a laminate before clinical testing. Eighty children from a rural area in Northern Ethiopia were fed edible, fortified hydrocolloid sponges carrying 4000 IU of vitamin A. The edible sponges were being tested as a means of supplementing preschool children in an area with endemic vitamin-A deficiency. Levels of vitamin A increased significantly following ingestion of the edible cellular solid suggesting its usefulness as a carrier of vitamin A for children. The sponge consisted of hydrocolloid matrices to which oil had been added by homogenization. After gelation and freeze-drying, a crunchy, chewable, cellular solid designed as "packaging" for the vitamin A was produced. Because it is void of flavor, odor and color, these characteristics can be controlled and incorporated during processing, to ensure broad acceptance by the targeted subjects. The product was studied for its mechanical (textural) properties to enable customized, affordable, stable packaging.

Vitamin A is an essential micronutrient involved in growth, epithelial maintenance, vision and reproduction (1), Vitamin-A deficiency (VAD) is a widespread problem, affecting mainly developing countries. Worldwide, 20 to 40 million children are estimated to be at least mildly vitamin-A deficient. VAD is the major cause of blindness among preschool children in many developing countries and also carries an increased risk of morbidity and mortality. Subclinical VAD has also been associated with high child morbidity and mortality and vitamin-A supplementation has been shown to reduce these statistics substantially (2). At present, there are three aproaches to dealing with the problem of VAD: a) biannual distribution of a high-level dose of vitamin A to preschool children in areas where VAD is a public-health priority; (b) horticultural and nutritional education, and (c) food fortification. However at this point, these approaches are only technologically feasible on an experimental basis in a number of countries due to their cost and the problem of selecting a suitable vehicle (a food item regularly eaten by the target group in sufficient quantities) (3), (d) One of the biggest obstacles to supplementing children with vitamin A is lack of compliance caused by taste.

In the rural area of Gondar, Ethiopia, 220 families were screened for vitamin-A status. Blood was obtained front 161 preschool children, 2–5 yrs of age. Following the first blood drawing, 80 children were randomly chosen to receive the fortified edible sponge monthly for 3 months. A field worker visited the houses of the preschool children every 2 weeks. Blood was drawn again after the 3-month period to determine vitamin-A levels. The study was approved by the ethics committee of the Gondar College of Medical Sciences. Reverse-phase high-pressure liquid chromatography (HPLC; GBC Co.), at a working pressure of 2.6 MPa, and a flow rate of 0.6 ml/min equipped with a Lichro Cart 125-4 column, filled with 100RP-18 of Merck and flushed with 20% (v/v) ethyl acetate/methanol (7) was used to detect vitamin-A levels during sponge formation and in the sera of the preschool children receiving the sponge.

The commercial food-grade alginate Keltone LV (Kelco, San Diego, Calif.) (mol wt. 70,000–80,000, 61% mannuronic acid and 39% guluronic acid content) was used to prepare the gels, which were liter freeze-dried for sponge production. The sodium-alginate powder (1% w/w), 1% (w/w) calcium hydrogen orthophosphate ($CaHPO_4$; (Riedel-deHaen, Seelze, Germany) and 1% sodium-hexa-metaphosphate (SHMP; BDH, Poole, England) were slowly added to cold (10° C.) distilled water, with constant stirring, to complete dissolution. A freshly prepared solution of 2% (1w) glucono-δ-lactone (GDL; Sigma, St. Louis, Mo.), was vigorously stirred into solution. Alginate-vitamin A gels were produced as above except that 500 ppm vitamin A, 1% soy oil, 500 ppm lecithin sodium saccharin and 50 ppm β-carotene were added by homogenization for 20 min at 700 bar (APV Rannie, model mini-lab type 8.30H). The vitamin A and the other additives (oil, emulsifier, color and artificial sweetener) were incorporated into the gum solution, to which a 2% (w/w) GDL solution was later added. The mixture was poured into a plastic container (10×10×8 cm ) and allowed to set. After 48 h, gels, were freeze-dried to produce the desired sponges.

Sponge Mechanical Properties and Porosity

The freeze-dried gets were compressed to ~80% deformation between parallel lubricated plates at a constant deformation (displacement) rate of 10 mm/min, using the Instron. The Instron's continuous voltage vs. time output was converted into a stress vs. Hencky's (natural) strain relationship using the following equations:

$$\sigma = F/A_o \quad (1)$$

$$\epsilon_H = \ln[H_o/(H_o - \Delta H)] \quad (2)$$

where σ and ε are stress and Hencky's strain, respectively, F is the momentary force, ΔH=Ho−H(t) is the momentary deformation, Ao and Ho are the original specimen's cross-sectional area and height, respectively, and H(t) is the height at time t. Since the cross-sectional area of a compressed solid sponge specimen rarely expands to any significant extent (1), the engineering and "true" stresses can be treated as equal for all practical purposes (4). The individual relationship were fitted to a compressibility model previously developed for the sigmoid stress-strain relationships of cellular solids (8, 9, 10):

$$\sigma = C_1 \epsilon / [(1 + C_2 \epsilon)(C_3 - \epsilon)] \quad (3)$$

where σ and ε are the stress and strain, respectively, and $C_1$, $C_2$ and $C_3$ are constants calculated by nonlinear regression of the Systat package. The constant $C_1$ is primarily a scale factor and has stress units. The constant $C_2$, dimensionless, is a measure of the shoulder's prominence in the stress-strain curve—that is, when $C_2=0$, the relationship has no shoulder and its slope increases monotonically. The constant $C_3$, also dimensionless, is a rough measure of the steepness of the stress-strain curve in the high-strain region. According to equation 3, when ε goes to $C_3$, σ tends to infinity, $C_3$ is determined largely by the strain level at which collapse of the open structure has been completed and most of the resistance to deformation has been shifted to the compacted solid cell-wall material. All mechanical tests were performed in duplicate.

The porosity of the sponge specimens was calculated as: P=1−(bulk/density/solid density) (11). Bulk density was (estimated by dividing the sample weight by its overall volume. The latter was measured by displacement using 150 to 200 μm diameter glass beads. Particle (solid) density was derived by dividing the sample weight by its particle volume, as determined by pycnometer (Multi-Pycnometer, Quantachrome,Syosset, N.Y.). Particle volume was determined at least twice with duplicate samples, by helium displacement at a working pressure of 2.1±0.1 atm. Following these pycnometer measurements, the same samples were used for the bulk-density determinations with the glass beads.

Scanning Electron Microscopy

SEM micrographs were obtained by the following procedure: a new double-edged razor blade was used to cut through the solid foams and expose the internal surface features. Single downward cuts were used to produce 1- to 2-mm thick slices of samples. A 1:1 (v/v) mixture of colloidal graphite in isopropyl alcohol and Ducco household cement was used as a conductive mounting adhesive. Sample pieces were mounted onto 10×10 mm aluminum SEM stubs and coated in a Polaron E5100 sputter-coating unit with a Peltier cooling stage. Samples were coated with approximately 50 nm of Au/Pd (60:40 w/w), and examined in a Jeol JSM 25S SEM at an accelerating voltage of 15 kV and a working distance of 48 mm.

Results

A typical stress-strain relationship in vitamin A sponges has been observed for vitamin A sponges. The average constants of equation 3 for typical stress-strain curves of alginate sponges with and without additives were calculated using a nonlinear regression based on minimizing the mean of the squared deviation. The compressibility parameters of these cellular solids with and without vitamin A were almost the same, namely: $C_1=1180\pm5$ kPa, $C_2$ (dimensionless)= $17.5\pm0.5$ and $C_3$ (dimensionless)=$1.75\pm0.03$ $R^2$ was 0.99–1.00. The vitamin-A sponges (dried alginate gels with additives) behaved like a typical cellular solid. The stress-strain relationships were of the sigmoidal type and were composed of the three regions detected for other cellular solids (5, 6). Both dried gels (the regular one and the vitamin A-sponge) behaved similarly (their only difference being the small addition of vitamin, color, artificial sweetener and emulsifier, which seemed to have no influence on the compressibility parameters).

The sponge's inner structure was studied by scanning electron microscopy. Scanning electron microscopy of the sponges (FIG. 8) revealed a structure composed of big openings ("cells"). The vitamin was assumed to be embedded within the solid walls of the matrix, thereby eliminating or minimizing the problem of oxidation and conferring slow-release properties. The porosity of the vitamin-A sponges was ~95%. It should be noted that since it is possible, at least in principle, to change the porosity of such cellular solids by adding other ingredients (i.e. increasing dry matter) (6), it is possible to change the rate of vitamin release in the intestines.

The average serum-retinol level for the whole population was 0.74 μmol/L: 14 children (8.6%) were vitamin-A deficient as defined by a serum-retinol concentration <35 μmol/L and 78 children (48%) had a low concentration (<0.70 μmol/L). Serum-retinol values for the study group which received the vitamin-A-containing sponge for 3 months were as follows: 39.0±20.6 μmol/L before intervention, 55.3±19.0 μmol/L after 3 months of treatment. Vitamin A levels increased significantly (p<0.001) following ingestion of the edible cellular solid, suggesting its usefulness as a carrier of vitamin A for children. In all cases but one, the levels of vitamin A in children who were below the normal range rose to normal following ingestion of the sponge. In one child, the level remained subnormal despite sponge ingestion. Of the 80 children assigned to receive the edible sponges, three children refuse to eat it. The other 77 ate the sponge all three times during the study period.

TABLE 3

COMPRESSIBILTY PARAMETERS OF FREEZE-DRIED GEL SPONGES WITH AND WITHOUT INTERNALLY PRODUCED GAS BUBBLES

| | Immersion time (h) | $C_1$ (kPa) | $C_2$ (-) | $C_3$ (-) | MSE[a] |
|---|---|---|---|---|---|
| Alginate 1% | 0 | 1180 | 18 | 1.8 | 104 |
| | 0.8 | 3520 | 56 | 2.0 | 21 |
| | 1.8 | 1690 | 36 | 1.8 | 16 |

[a]MSE mean square error. $C_1$, $C_2$ and $C_3$ are constants from eq #3

The constants $C_1$, $C_2$ and $C_3$, as previously mentioned, were determined by a nonlinear regression procedure that is based on minimizing the mean of the squared deviations.

TABLE 4

PHYSICAL PROPERTIES OF SOYA VEGETABLE OIL*

| | |
|---|---|
| Specific gravity (kg/m³) | 0.91 |
| Iodine number | 120–141 |
| Refractive index | 1.467–1.470 |
| Saponification number | 188–195 |
| % Unsaponified matter | 0.5–1.6 |
| % Free fatty acids | 0.02–0.1 |
| Peroxide value (meq/kg) | 1.0 max |
| % Moisture | 0.1 max |
| Melting point | −21° C. ± 1 |
| Smoking point | 450–460° F. |
| Flash point | 635–645° F. |
| Fire point | 700–710° F. |

*Provided by the manufacturer

TABLE 5

COMPRESSIVE MECHANICAL PROPERTIES OF ALGINATE SOY-OIL GELS*

| % Oil (w/w) | Failure stress (kPa) | Hencky's strain (-) | Deformability modulus (kPa) | $R^2$ of σ vs. ε |
|---|---|---|---|---|
| 0 | 13.1 ± 0.2 | 0.65 ± 0.02 | 10.3 ± 0.3 | 0.993 |
| 10 | 11.9 ± 0.6 | 0.55 ± 0.08 | 8.5 ± 0.5 | 0.981 |
| 20 | 9.5 ± 0.5 | 0.54 ± 0.04 | 6.0 ± 0.6 | 0.988 |
| 30 | 3.9 ± 0.1 | 0.50 ± 0.01 | 3.4 ± 0.6 | 0.996 |
| 40 | 3.6 ± 0.4 | 0.47 ± 0.02 | 2.1 ± 0.1 | 0.991 |

*Each result represents the average of six determinations ± SD.

TABLE 6

OIL CONCENTRATION IN OIL-ALGINATE GELS AND SPONGES

| Oil content within alginate gels (%, w/w) | Oil content in gels after heat treatment (%, w/w) | Oil in sponges (%, w/w) |
|---|---|---|
| 0 | 0 | 0 |
| 10 | 6 | 40 |
| 20 | 12 | 57 |
| 30 | 18 | 66 |
| 40 | 28 | 75 |

TABLE 7

MODEL CONSTANTS OF NON-LINEAR REGRESSION IN
COMPRESSION STRESS-STRAIN RELATIONSHIPS
OF OIL-FREEZE DRIED

| Oil in gels (%, w/w) | $C_1$ (MPa) | $C_2$ (-) | $C_3$ (-) | MSE[a] (× $10^{-6}$) |
|---|---|---|---|---|
| 0 | 0.32 | 444 | 0.94 | 1.39 |
| 10 | 0.19 | 65 | 0.93 | 1.35 |
| 20 | 4.10 | 1719 | 0.88 | 3.60 |
| 30 | 0.01 | 5 | 0.76 | 0.78 |
| 40 | 0.52 | 304 | 0.68 | 0.72 |

[a]MSE mean square error. $C_1$, $C_2$ and $C_3$ are constants from eq. #3

References

Attenburrow, G.E., Goodband, R.M., Tylor, L.J., Lillford, P.J.'J. Cereal Science 9, 61-70, 1989.

Gibson, L.J. and Ashby, M.L. (1988) Cellular Solids: Structure and Properties; 357 pages, Pergamon Press, Oxford, UK.

Nussinovitch, A., Velez-Silvestre, R. and Peleg, M. (1993). Compressive characteristics of freeze-dried agar and alginate gel sponges. Biotechnology Progress, 9, 101-104.

Nussinovitch, A. (1995). Compressive characteristics of hydrocolloid sponges. The eighth international conference and industrial exhibition on gums and stabilizers for the food industry, July 1-14, The North East Wales Institute, Cartrefle College, Wrexham, CLWYD, UK.

Nussinovitch, A., Peleg, M. and Normand, M.D. (1989). A modified Maxwell and a non-exponential model for characterization of the stress relaxation of agar and alginate gels. J. Food Science, 54, 1013-1016.

Nussinovitch, A., Nussinovitch M., Shapira, R., Gershon, Z., Food Hydrocolloids 8 (3-4), 361-372, 1994.

Nussinovitch, A., Peleg, M., J. Texture Studies 21, 51-60, 1990.

Peleg, M. (1982) In: Physical Properties of Foods, chapter 10, (Peleg, M. and Bagley, E.B.eds.) pp. 293-321. Avi Publishing Company Inc., Westport, CT.

Rahmathullah, L. Underwood, B.A., Thulasiraj, R.D., Milton, R.C., Ramaswamy, R., Rahmathullah, G., Babu, G. (1990) Reduced mortality among children in southern India receiving a small weekly dose of vitamin A. NEJM 323: 929-35.

Sklan, D. & Ayal, A. (1989) Effect of saturated fat on growth, body fat composition and carcass quality in chicks. Br. Poult. Sci. 30: 407-411.

Sommer, A. (1992) Vitamin A: Its effect on childhood sight and life. Scan. J. Nutr. (Supp 27): 6-67.

Swyngedau, S., Nussinovitch, A., Roy, I., Peleg, M. and Huang, V. (1991) J. Comparison of four models for the compressibility of breads and plastic foams. Food Science, 56, 756-759.

Swyngedau, S., Nussinovitch, A. and Peleg, M. (1991a). Models for the compressibility of layered polymeric sponges. Polymer Engineering Science, 31, 140-144.

Viteri, E.F., Alvarez, E., Batres, R., Torun, B., Pineda, O., Mejia, L.A. & Sylvi J.(1995). Fortification of sugar with iron sodium ethlenediaminotetraacetate (FeNaEDTA) improves iron status in a semirural Guatemalan population. Am.J. Clin. Nutr. 61: 1153-1163.

What is claimed is:

1. A sponge having predetermined characteristics of water absorption, biodegradability and pore size and structure, said sponge being produced by:
    a) expanding a hydrocolloid gel with a gas wherein said gas becomes entrapped as bubbles within the matrix of said gel, and wherein said gel remains unbroken, followed by
    b) drying said expanded gels,
    wherein said hydrocolloid gel is selected from the group consisting of agar, carrageenan, gelatin, alginate, pectin, gellan, kunjak mannan, xanthan locust bean, and combinations thereof.

2. A sponge according to claim 1, comprising edible components.

3. A sponge according to claim 2, containing a predetermined quantity of a high-calorie content ingredient.

4. A sponge according to claim 1, containing a plasticizer.

5. A sponge according to claim 4, where the plasticizer is an edible plasticizer.

6. A sponge according to claim 5, where the plasticizer is glycerol, sorbitol or another suitable polyol.

7. A sponge according to claim 3, where the sponge contains a sugar or sugar substitute, optionally with a flavoring agent or taste enhancer.

8. A sponge according to claim 1, having a specific density from about 0.01 g/cm to about 0.4 g/cm.

9. A sponge according to claim 3, wherein said high-calorie content ingredient is selected from the group consisting of fats, sugars, oils and alcohols.

10. A process for the production of a sponge, comprising:
    a) expanding a hydrocolloid gel with a gas, wherein said gas becomes entrapped as bubbles within the matrix of said gel, and wherein said gel remains unbroken, followed by
    b) drying said expanded gel;
    c) incorporating at least one fermenting microorganism in said gel;
    d) contacting said gel with a nutrient solution containing nutrients for said at least one fermenting microorganism, thereby forming carbon dioxide and forming said sponge.

11. A process for the production of a sponge, comprising:
    a) incorporating an acid into a hydrocolloid gel;
    b) placing said hydrocolloid gel in calcium carbonate;
    c) producing a gas by diffusion of said calcium carbonate into said hydrocolloid gel and decomposition by said acid; and
    d) expanding said hydrocolloid gel with said gas wherein said gas becomes entrapped as bubbles within the matrix of said gel, and wherein said gel remains unbroken, followed by
    e) drying said expanded gel,
    wherein said hydrocolloid gel is selected from the group consisting of agar, carrageenan, gelatin, alginate, pectin, gellan, kunjak mannan, xanthan locust bean, and combinations thereof.

* * * * *